United States Patent [19]

Papaioannou

[11] Patent Number: 5,722,406
[45] Date of Patent: Mar. 3, 1998

[54] DEVICE FOR CARRYING OUT OPTICAL MEASUREMENTS IN TURBID MEDIA

[75] Inventor: Dimitrios Papaioannou, Eindhoven, Netherlands

[73] Assignee: U.S. Philips Corporation, New York, N.Y.

[21] Appl. No.: 618,889

[22] Filed: Mar. 20, 1996

[30] Foreign Application Priority Data

Mar. 23, 1995 [EP] European Pat. Off. .............. 95200725

[51] Int. Cl.⁶ ...................................................... A61B 5/05
[52] U.S. Cl. ...................... 128/653.1; 128/664; 128/665; 356/432; 250/330
[58] Field of Search ...................... 128/653.1, 664, 128/665, 633; 356/39, 432, 433, 445, 446, 447, 448; 250/330, 358.1

[56] References Cited

U.S. PATENT DOCUMENTS

| | | | |
|---|---|---|---|
| 5,416,582 | 5/1995 | Knutson et al. | 128/665 |
| 5,424,843 | 6/1995 | Tromberg et al. | 356/442 |
| 5,497,769 | 3/1996 | Gratton et al. | 128/664 |
| 5,582,168 | 12/1996 | Samuels et al. | 128/633 |
| 5,625,458 | 4/1997 | Alfano et al. | 128/633 |

FOREIGN PATENT DOCUMENTS 9325145   12/1993   WIPO.

OTHER PUBLICATIONS

"Digital Parallel Acquisition in Frequency Domain Fluorimetry" B. Feddersen et al, Rev. Sci. Instrum. 60 (9) Sep. 1989, pp. 2929–2936.

*Primary Examiner*—Brian L. Casler
*Attorney, Agent, or Firm*—Jack D. Slobod

[57] ABSTRACT

A device for localizing an object 118 in a turbid medium (111), includes a laser (100) which is used for generating amplitude modulated light that is conducted into a turbid media (111), and a detection unit (107) for measuring the amplitude-modulated light emanating from the turbid media. A signal processing unit (109) measures a phase and amplitude from the detector signal (115). Based on the insight that the accuracy of the measured phase is influenced by higher harmonics present in the detector signal (115), the accuracy of the phase detection is improved by reducing such higher harmonics. This is achieved by reducing the higher harmonics in the amplitude modulated light from the laser (100) by utilizing a two-mode laser.

20 Claims, 5 Drawing Sheets

DEVICE FOR CARRYING OUT OPTICAL MEASUREMENTS IN TURBID MEDIA

BACKGROUND OF THE INVENTION

1. Field of the Invention

The invention relates to a device for localizing an object in a turbid medium, comprising a laser for generating radiation which is amplitude modulated with a modulation frequency, and a detection unit for measuring the amplitude-modulated radiation from the turbid media.

2. Description of the Related Art

A device of this kind is known from the international Patent Application WO 93/25145. In the known device the amplitude-modulated radiation is coupled into the turbid medium via one or more entrance windows. The radiation, which passes the turbid media, is conducted to the detector unit via a displaceable exit window. The propagation of the amplitude-modulated radiation in the turbid medium can be explained by photon density principles. An amplitude and a phase of these photon density waves can be measured at the area of the exit window by means of the detector. The measured phase and the measured amplitude are subsequently used to localize the object in the turbid medium. Furthermore, in the known device the amplitude-modulated radiation is generated by means of a laser diode, in which the electric current is modulated, or by means of a laser with an electro-optic modulator. Therefore, a modulating signal whereby the laser diode or the electro-optic modulator is controlled is present in the device. This modulating signal also serves as a reference signal for the phase measurement. Further development of the known device may result in the localization of tumours in biological tissues, so that it can be applied in medical diagnostics in addition to, for example X-ray mammography or MRI.

It is a drawback of the known device that the object cannot be localized when the scattering coefficient of the object hardly deviates from that of the turbid medium.

SUMMARY OF THE INVENTION

It is inter alia an object of the invention to provide a device whereby the localization of the object can be improved. To this end, the device in accordance with the invention is characterized in that the laser comprises means for suppressing higher harmonics in the amplitude-modulated radiation. In the context of the present application radiation is understood to mean electromagnetic radiation having a wavelength roughly between 200 nm and 1200 nm. It appears that localizing an object is dependent on the phase measurement accuracy that can be achieved by means of this device. It has been found that in the known device sufficient high accurate phase measurement can hardly be carried out because of the large higher harmonics component in the detector signal. In accordance with the invention, the higher harmonics component in the amplitude modulation of the detector signal is strongly reduced by suppression of the higher harmonics in the amplitude-modulated radiation. This enables more accurate phase measurement.

Even though lasers with strong higher harmonics suppression are known per se, it is not obvious to replace a laser comprising an external electro-optic modulator or a amplitude modulated laser diode in the known device by a laser with strong higher harmonics suppression, because problems occur then in obtaining a reference signal for the phase measurement. By the replacement of the external modulated lasers by the laser with strong higher harmonics suppression, the reference signal, which is deviated from the modulating signal, is no longer coupled to the amplitude modulation of the laser. As a result, the reference signal cannot follow a phase jump, if any, in the amplitude modulation of the laser, so that exact phase measurement is no longer possible under all possible measurement conditions.

Furthermore, inter alia from the article "Digital parallel acquisition in frequency domain fluorometry" by A. Brett et al, published in Review of Scientific Instruments, No. 60 (9), September 1989, it is known that higher harmonics in an amplitude-modulated signal originating from a detector introduce a large error in the measured signal phase, and also that the suppression of higher harmonics in the amplitude modulation of the detector signal allows for improved phase measurement. The cited article also proposes a digital filtering method for suppressing higher harmonics in the detector signal with a view to improve the accuracy of the phase measurement of the amplitude modulation. It is a drawback of the digital filtering method, however, that it introduces an undesirable delay in the measurement. In accordance with the invention there is obtained a detector signal in which the higher harmonics have been substantially suppressed as a result of the use of amplitude-modulated laser radiation in which the higher harmonics have been strongly suppressed, thus enabling improved phase measurement, when no phase jump occurs in the A.M. laser radiation.

A first embodiment of the device in accordance with the invention is characterized in that the laser is a two-mode laser and the modulation frequency equals a difference frequency between the two laser modes. This step results in a suppression of approximately 65 dB of the first harmonic in the amplitude-modulated radiation of the laser, whereas in the known devices, using an external modulator, the suppression of the first harmonic in the amplitude-modulated radiation amounts to approximately 25 dB.

A further embodiment of the device in accordance with the invention is characterized in that the device comprises means for generating a phase reference from the laser radiation. This phase reference is a reference signal used in the phase measurement. This step couples the phase and the frequency of the reference signal to the phase and the frequency of the amplitude modulation of the laser radiation so that measurements under all possible conditions are possible, even when phase jumps occur in the A.M. laser radiation.

A further embodiment of the device in accordance with the invention is characterized in that the higher harmonics suppressing means are formed by at least one etalon. A spectrum of modes of slightly different frequency occurs in the laser cavity. The etalon selects two modes in the laser cavity for which the difference between the associated frequencies corresponds to the desired amplitude modulation of the laser. The amplitude modulation of the laser subsequently takes place by interference of these selected modes.

A further embodiment of the device in accordance with the invention is characterized in that the device comprises optical beam splitter for creating secondary radiation sources from the laser radiation. It is thus achieved that the harmonics and also the phase relationships of the secondary radiation sources are equal, so that phase jumps are precluded in the modulation of a single secondary radiation source and hence suitable phase measurement is possible.

A further embodiment of the device in accordance with the invention is characterized in that an optical path difference induces a phase shift between two secondary radiation sources. This step defines the direction of the wave front of the photon density waves by adjustment of the phase of each secondary radiation source relative to the other secondary radiation sources.

A further embodiment of the device in accordance with the invention is characterized in that the secondary radiation sources are subdivided into a first group and a second group, the amplitude modulation of the radiation to be generated by the first group of radiation sources exhibiting a phase difference relative to the amplitude modulation of the radiation to be generated by the second group of radiation sources. As a result of this step, two photon density waves exhibiting a phase difference relative to one another are generated in the turbid medium. When the photon density waves are in phase opposition, a strong spatial phase variation is obtained, thus enhancing the sensitivity of the phase measurement and hence the detection of objects.

A further embodiment of the device is characterized in that secondary radiation sources are formed by the optical conductor ends coupled to the optical beam spitters. As a result of this step, the secondary sources can be optically coupled to the laser via optical conductors, for example optical fiber or a system of geometrical-optical components. The use of optical fiber often the advantage that they can be simply introduced into the turbid medium. Moreover, the desired phase relationships of the secondary radiation source can be simply established by adaptation of the length of the optical fiber.

For the measurement of the phase in the device in accordance with the invention use is preferably made of a detection unit which is characterized in that an intermediate-frequency signal is derived from the phase reference. In order to obtain low-frequency signals for the phasemeter in a known phase measurement the reference signal as well as the measurement signal is multiplied by an intermediate-frequency signal. This produces sum and difference signals of the intermediate-frequency signal relative to the measurement signal as well as the reference signal. From these signals only the two low-frequency difference signals are applied to the phasemeter. The phasemeter, however, is affected by a frequency variation of the two signals. This frequency variation may occur due to a small frequency variation of the amplitude modulation of the laser. When the intermediate-frequency signal is derived from the reference, the intermediate-frequency signal follows the frequency of the reference, so that the frequency of the low- frequency difference signals applied to the phasemeter is substantially constant, thus reducing the measurement error in the phasemeter.

The above and other, more detailed, aspects of the invention will be described in detail hereinafter, by way of example, with reference to the drawing.

DETAILED DESCRIPTION OF THE PREFERRED EMBODIMENTS

Figure 1:
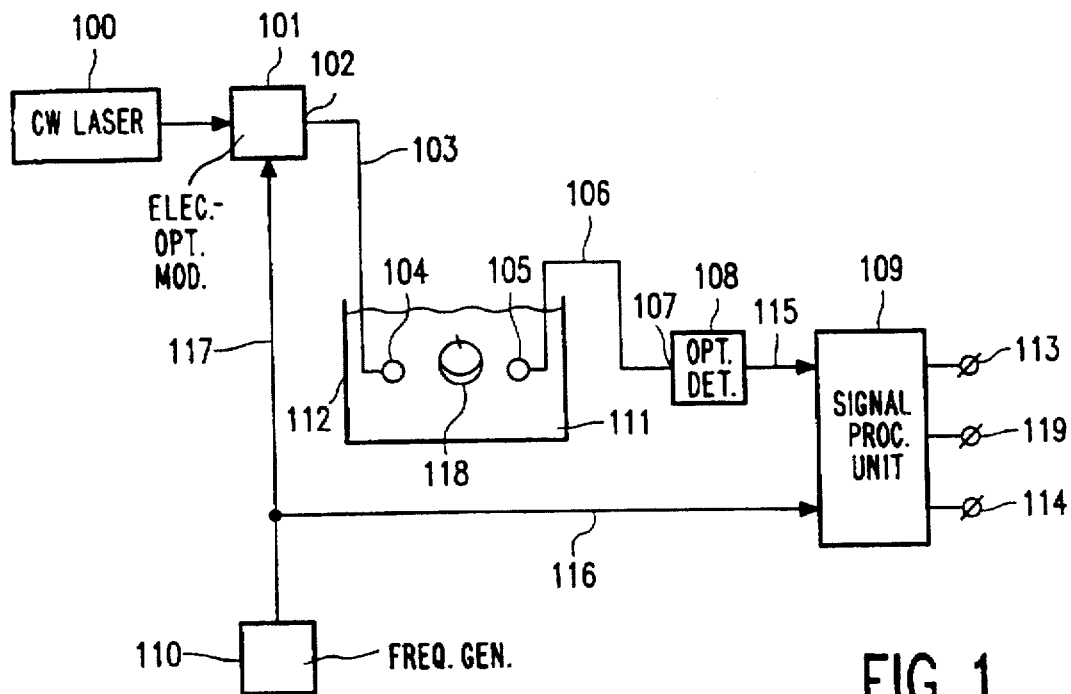
FIG. 1 shows a first known device for carrying out optical measurements in a turbid medium.

FIG. 1 shows a known device for carrying out optical measurements in a turbid medium. This device is known from the cited Patent Application WO93/25145. The device comprises a CW laser 100 with an electro-optical modulator 101, a first optical conductor 103, for example an optical fibre, which is coupled to the electro-optical modulator 101 by way of a first end 102 and which is arranged in or on a turbid medium 111 by way of a second end which constitutes a secondary light source 104. In an experimental set-up the turbid medium is formed, for example by a 1% Intralipid solution in a container 112. The concentration of the Intralipid solution is measured with respect to pure Intralipid, and not the commercial available Intralipid-10% product. This product is in fact a 10% solution of pure intralipid. The product used in the experiments corresponds to the commercial product diluted by 10 times. In the envisaged medical application the turbid medium is formed by biological tissue, for example a female breast or a neonatal infant's head. Furthermore, a first end of a second optical conductor 106, constituting the aperture 105 of a detecting plane, is arranged in the turbid medium 111 opposite the light source 104. The second end 107 of the second optical conductor 106 is coupled to an optical detector 108, for example a photodiode or a photomultiplier tube. The light signal is converted into an electric detector signal 115 in the optical detector 108. The detector signal 115 is guided to a signal processing unit 109. In the signal processing unit 109 a signal phase, a signal amplitude and a DC-level are measured relative to a reference signal 116. The measured phase, the measured amplitude and the measured DC-level are available as voltages on the terminals 113, 114 and 119.

For the execution of measurements the light of the laser 100 is amplitude modulated by way of the electro-optical modulator 101 driven by a modulation signal 117 of a frequency of, for example 219 MHz which is generated by the frequency generator 110. The frequency generator 110 delivers also a reference signal 116. Subsequently, the light of the laser is guided into the turbid medium 111 via the electro-optical modulator 101 and the optical conductor 103. The intensity of the amplitude-modulated light in the turbid medium 111 is described by photon density waves of a wavelength $$\lambda = \left( \frac{4\pi c/n}{3\mu_s} \right)^{1/2},$$

in which f is the modulation frequency, $\mu_s$ is the scattering coefficient, n is the refractive index and c is the velocity of light. An object 118, for example a sphere, arranged in the turbid medium between the light source 104 and the detector aperture 105 will induce a deviating scattering of the light. Such deviating scattering of the light causes a deviation in the wave front of the photon density wave, so that an deviation in amplitude and phase occurs at the area of the detector opening 105.

For the localization of objects in the turbid medium the light source 104 as well as the detector aperture 105 are displaced synchronously in small steps in the turbid medium 111, the phase of the photon density wave being measured after each step. If in a given position of the light source 104 and the detector aperture 105 a phase is measured, which deviates from a reference phase, than an object is present between the light source 104 and the detector opening 105, the scattering and/or the absorption coefficient of said object deviating from the scattering and/or absorption coefficient of the turbid medium. Therefore, the precision of object localization is dependent on the sensitivity of the phase measurement.

The localization of objects in the turbid medium also utilizes an arrangement which is also known from the cited Patent Application WO93/25145. This arrangement constitutes several light sources, which light sources are subdivided into two groups, the amplitude modulation of the first group of light sources being in phase opposition with the amplitude modulation of the second group of light sources. As a result, two photon density waves in phase opposition arise in the turbid medium and an acute phase transition occurs between the first photon density wave and the second photon density wave. Because of this acute phase transition, a small variation of the scattering coefficient in an object will cause at the location of the phase reversal a phase deviation greater than the phase deviation caused when only a single photon density wave is used. Consequently, the device utilizing two photon density waves in phase opposition has a sensitivity superior to that of the device described with reference to FIG. 1.

Figure 2:
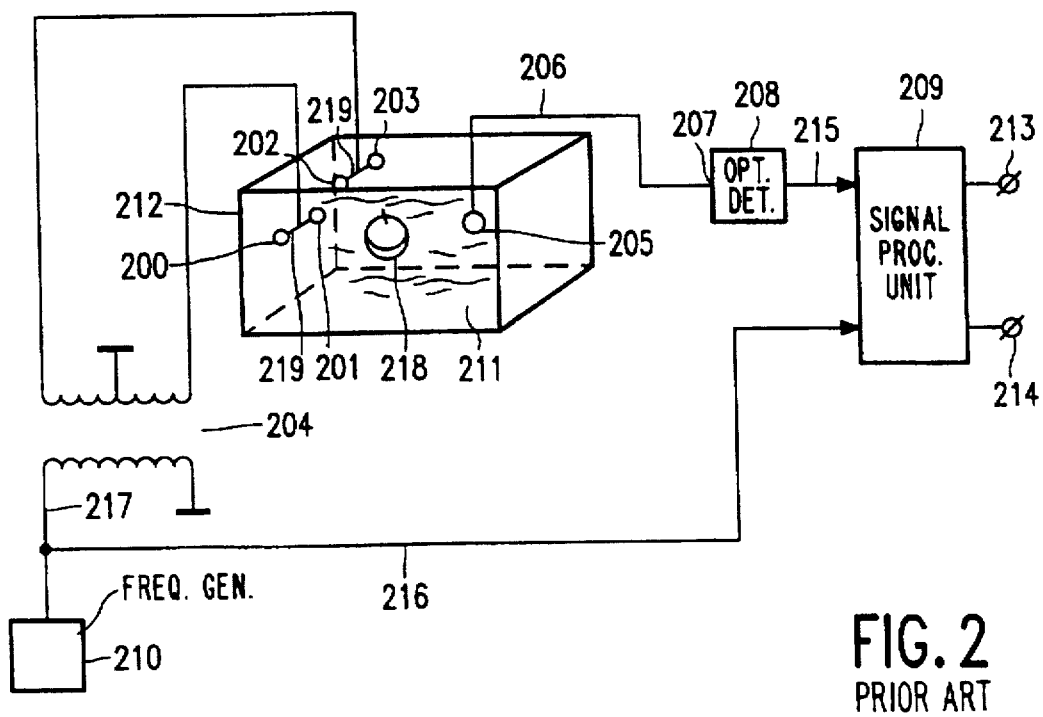
FIG. 2 shows a second known device, which comprises two groups of secondary light sources.

FIG. 2 shows the known set-up as described in the cited Patent Application WO93/25145. The light sources, for example laser diodes, are in this case subdivided into two groups of two laser diodes each, i.e. a fast group comprising the laser diodes 200, 201 and a second group laser diodes comprising the laser diodes 202, 203. Also two groups, each comprising one laser diode or two groups, each group comprises four laser diodes, are possible configurations of the light sources. The laser diodes 200, 201 of the first group are phase modulated and the laser diodes 202, 203 of the second group are modulated in phase opposition by means of the circuit 204, which controls the electric current through the laser diodes, and a modulation signal 217 of a frequency of, for example 219 MHz. The modulation signal 217 is supplied by a frequency generator 210. The laser diodes 200, 201, 202, 203 are mounted on a support 219 and arranged in a turbid medium 211. In an experimental set-up the turbid medium is formed, for example by a 1% Intralipid solution in a container 112. In the envisaged medical application the turbid medium is formed by biological tissue, for example a female breast or a neonatal infant's head. In this application the laser diodes and the detector are place opposite each other against the breast or the infants head. In the experimental set-up the four laser diodes 200, 201,202 and 203 are arranged in line. The distance between adjacent laser diodes mounts to a few centimeters, for example 2.5 cm. The first end 205 of the optical conductor 206, for example an optical fiber, constituting the aperture 205 of a detector plane, is arranged at some distance, for example 5 cm, on a central perpendicular plane between the first group of laser diodes 200, 201 and the second group of laser diodes 202, 203 in the turbid medium 211. The second end 207 of the optical conductor 206 is coupled to an optical detector 208. The optical detector 208 converts the light signal into a detector signal 215. The detector signal 215 is applied to a signal processing unit 209. A reference signal 216 is supplied to the signal processing unit 209. This reference signal 216 is derived from the modulation signal 217. Subsequently, the signal processing unit 209 measures a phase and an amplitude which are available for further processing as voltages on the terminals 213 and 214.

When the intensities of the laser diodes 200, 201, 202 and 203 are equal, the phase transition in the turbid medium will arise in the central perpendicular plane between the first group of laser diodes 200, 201 and the second group of laser diodes 202, 203. This phase transition is measured via the detector aperture 205. For the localization of objects, for example the laser diodes 200, 201,202, 203 and the detector aperture 205 are synchronously displaced in small steps in or along the turbid medium 111, the phase of the photon density wave being measured after each step. An object 218 present between the laser diodes 200, 201, 202, 203 and the detector aperture 205 will cause a deviating wave front due to deviating scattering of the light, so that the phase transition is shifted and a phase variation is measured by the signal processing unit 109.

The localization of objects causing only a small scattering deviation requires a sensitive phase measurement. The sensitivity of the phase measurement in both known devices, however, is limited. It has been found that this is due to insufficient suppression of higher harmonics of the modulation frequency in the detector signal. According to the invention it has been found that the phase measurement can be improved by utilizing a laser with strong higher harmonics suppression. To this end, in the set-ups described with reference to the FIGS. 1 and 2 the external modulated lasers are replaced by an amplitude-modulated laser, for example an adapted Ti-sapphire laser Model 3900 as available from Spectra Physics.

Figure 3:
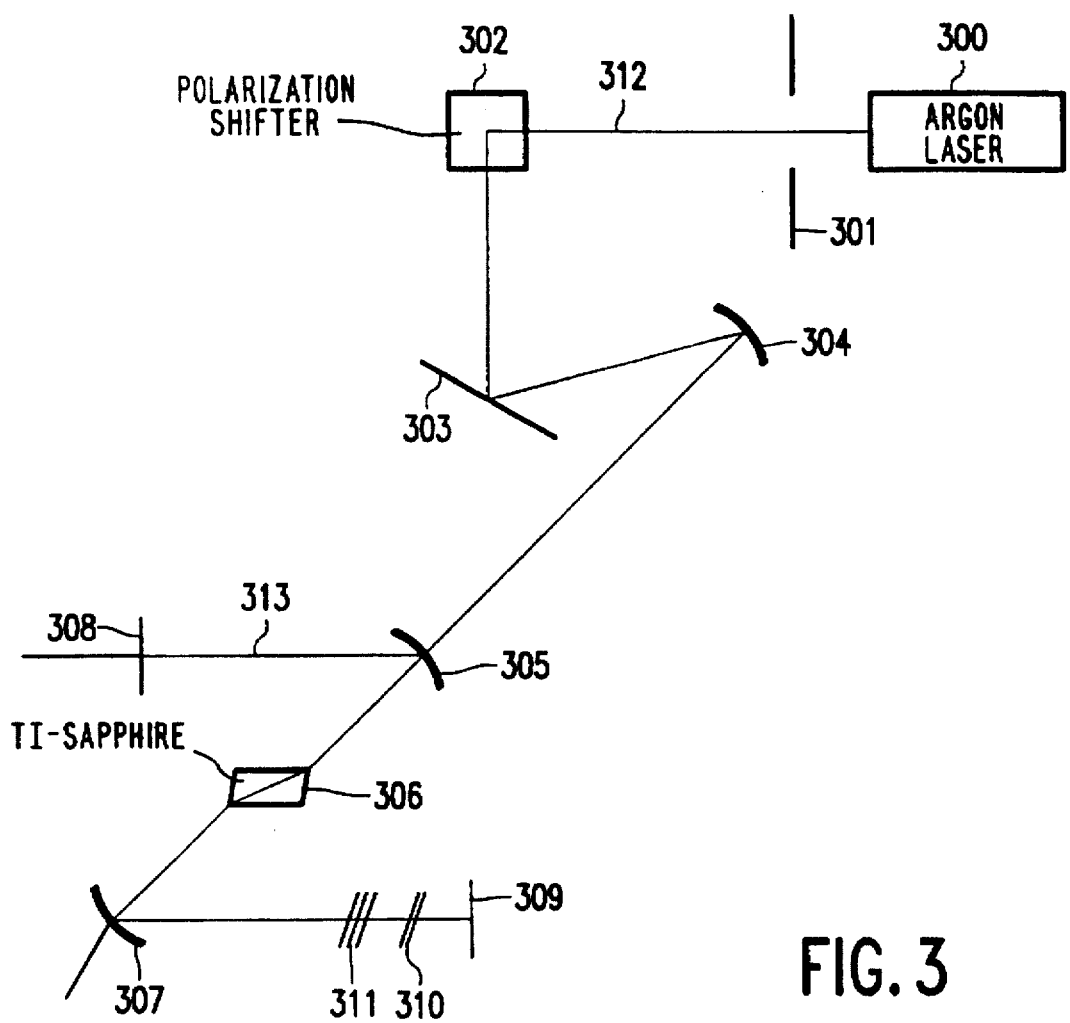
FIG. 3 shows diagrammatically the construction of a laser with strong higher harmonics suppression.

FIG. 3 shows a diagram of the adapted Ti-sapphire laser based on said type Model 3900. A pumping beam 312 is generated by means of an argon laser 300. The pumping beam 312 is guided to a pumping focus mirror 304 via a diaphragm 301, a polarization shifter 302 and a flat pumping beam mirror 303. Subsequently, the pumping beam 312 is focused by the pumping focus mirror 304 via the partly transparent folding mirror 305 on the Ti-sapphire 306. The remaining pumping beam 312 is drained via a partly transparent folding mirror 307. In the laser cavity formed between a first mirror 308 and a second mirror 309 a second laser beam 313 is generated by stimulated emission in the Ti sapphire 306. This second laser beam 313 is guided to the measurement set-up via the partly transparent first mirror 308. The second laser beam 313 contains a frequency spectrum of various adjacent modes. The frequency difference $\Delta v$ between two adjacent modes in this spectrum is determined by $\Delta v = v/2d$, in which v is the velocity of light in the medium and d is the optical path, which is the geometrical length multiplied by the refractive index, between the first mirror 308 and the second mirror 309. Two adjacent modes are then selected by arranging a birefringent filter 310 and an etalon 311 between the first mirror 308 and the second mirror 309, thus producing a laser beam which is amplitude modulated with a frequency of 219 MHz. It is also possible to apply an dedicated etalon, which selects more than two light modes having adjacent frequencies so that, in addition to an amplitude modulation of 219 MHz, amplitude modulations of 657 MHz occur. This higher modulation frequency has the advantage of providing a higher resolution in exchange of a lower penetration depth in the turbid media.

Figure 4:
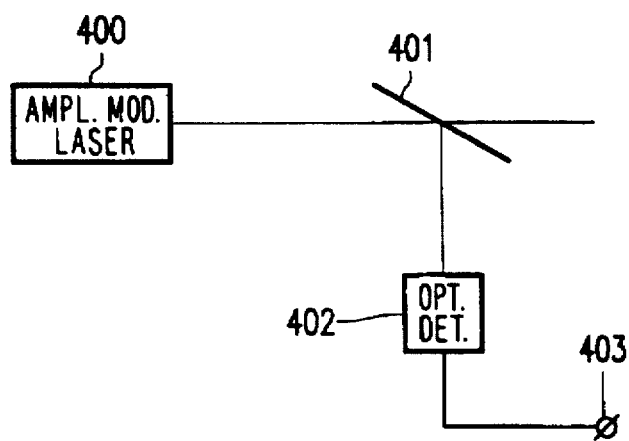
FIG. 4 shows a modification for deriving a reference signal.

In addition to the replacement of the laser by the amplitude-modulated laser, it is also necessary to adapt the signal processing unit 109 in a set-up in accordance with the invention, because the reference signal is no longer coupled to the amplitude modulation of the laser. A reference signal can be derived, for example from the output signal of the laser, as shown in FIG. 4.

Figure 5:
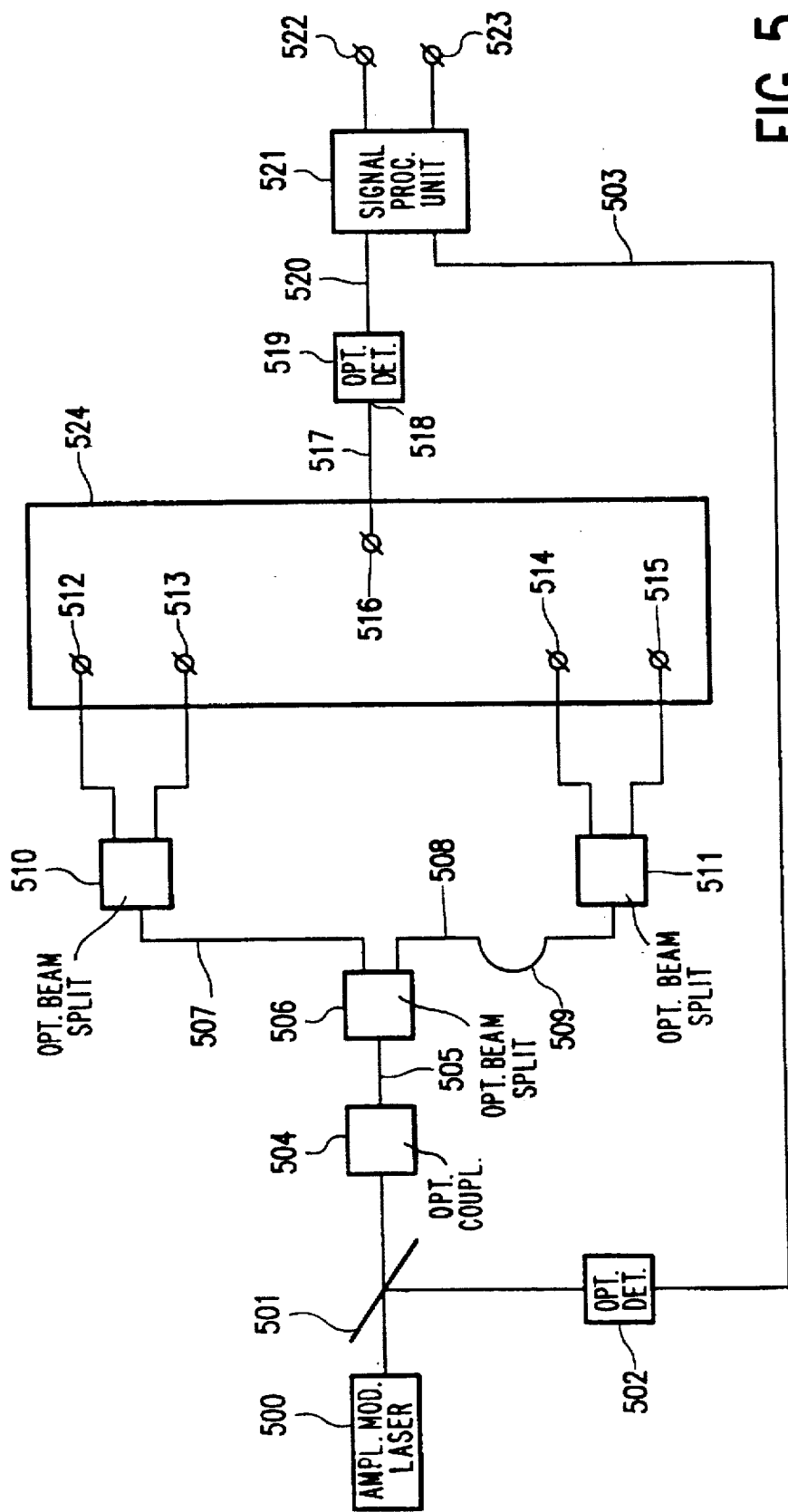
FIG. 5 shows a modification for deriving two groups of light sources which are in phase-opposition.

An optical beam splitter 401 is used to guide a part of the amplitude-modulated light from the laser 400 to a second optical detector 402. This optical detector 402, for example a photodiode, converts the splitted light beam in a reference signal 403. Moreover, in an embodiment using four laser as described in FIG. 2, the laser diodes 200, 201, 202 and 203 could be replaced by an amplitude-modulated laser, wherefrom four secondary laser diodes are derived by means of optical beam spitters, as is shown in FIG. 5.

The amplitude-modulated light beam of the laser 500 is split into two parts by means of an optical beam splitter 501. A reference signal 503 is converted from the first light beam, amounting to for example 10% of the total light intensity, by means of an optical detector 502. The second light beam is coupled into an optical conductor 505, for example an optical fiber, via an optical coupler 504. The optical conductor 505 is connected to a second optical beam splitter 506. The incoming light is again split into two light beams of equal intensity by means of the second optical beam splitter 506. From the second optical beam splitter 506 the first beam is guided to a third optical beam splitter 510, which comprises two optical fibre outputs, via the optical conductor 507. The third optical beam splitter 510 again splits the light into two parts of equal intensity, so that two secondary light sources 512, 513 are formed at the ends of the optical fibers. The second beam, originating from the optical splitter 506, is guided to a fourth optical beam splitter 511 via an optical conductor 508 having an additional length 509. Because of the additional length 509, a phase shift of 180 degrees occurs in the amplitude modulation of the light guided to the fourth optical beam splitter 511. The fourth optical beam splitter 511 also creates two light sources 514 and 515, from which light sources the amplitude modulated light is in phase opposition relative to amplitude modulated light of the light sources 512 and 513. The light sources 512, 513, 514 and 515 are arranged in the turbid medium 524. In the turbid medium 524 there is also arranged the end 516 of the optical conductor 517 whose second end 518 is coupled to the optical detector 519, so that light is guided from the turbid medium 524 to the optical detector 519. The optical detector 519 generates a detector signal 520 from the light signal. Also provided is a signal processing unit 521 which measures the phase of the detector signal 520 relative to the reference signal 503. The phase as well as the amplitude of the detector signal are available for further processing on the outputs 522, 523 of the signal processing unit 521.

Figure 6:
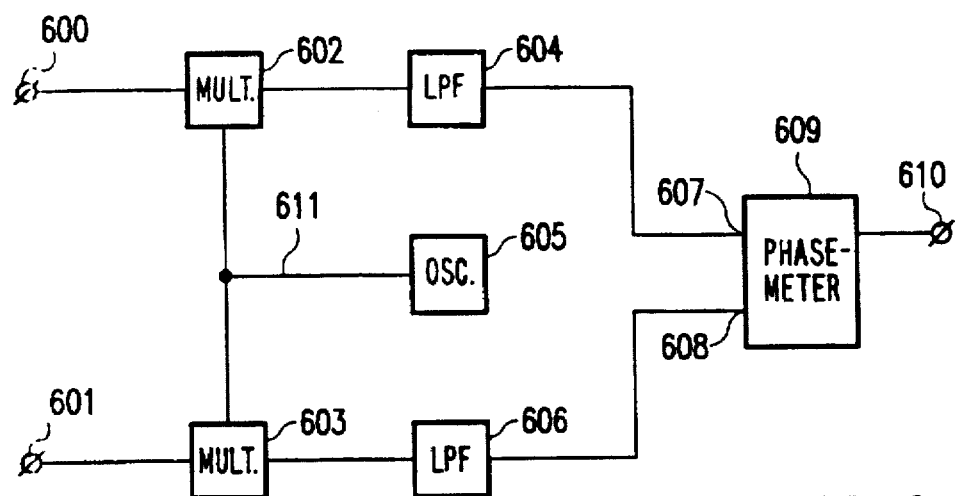
FIG. 6 shows a known phase detection unit.
Figure 7:
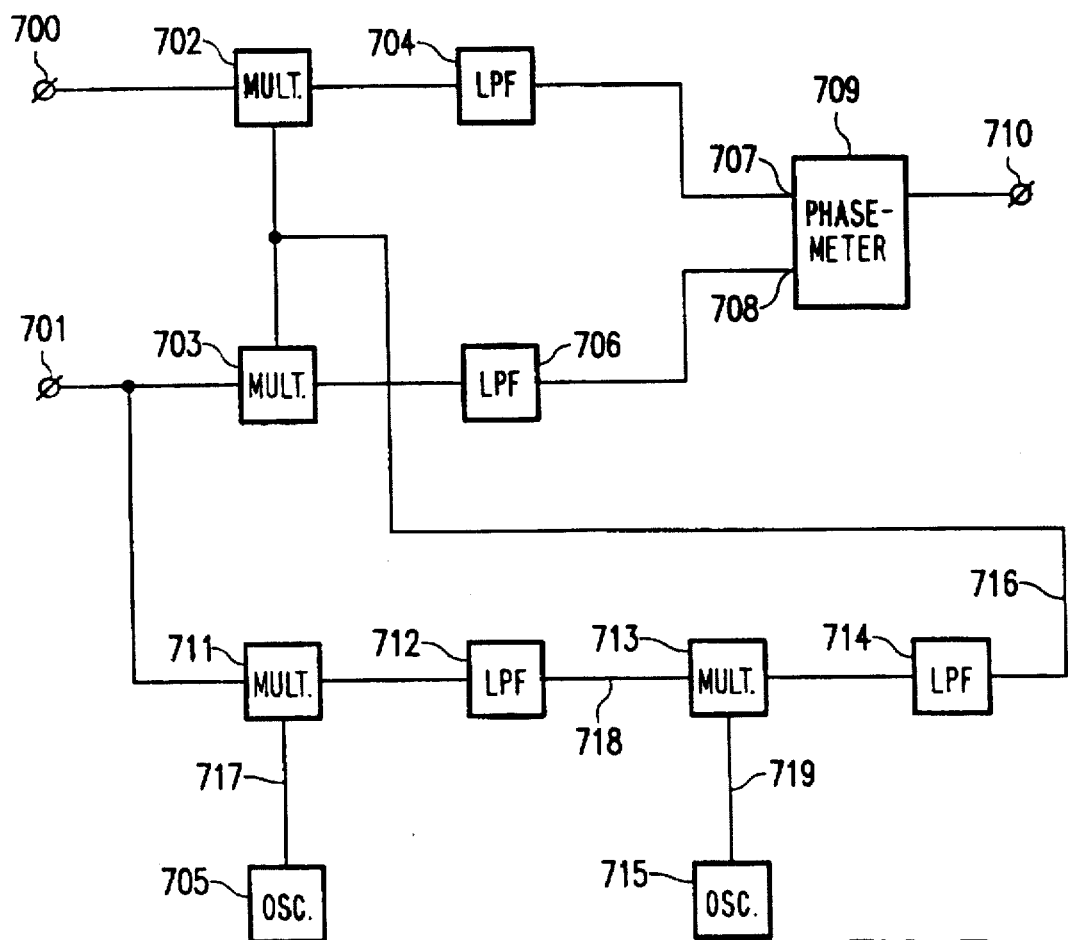
FIG. 7 shows an improved phase detection unit in accordance with the invention.

The measurement of the phase can be further improved in accordance with the invention by coupling the frequency of the intermediate-frequency signal to the frequency of the reference signal derived from the amplitude-modulated laser light, as will be illustrated by FIGS. 6 and 7.

FIG. 6 shows the construction of a known phase detection unit of the signal processing unit 109 for measuring the phase of the detector signal. In the known phase detection unit an intermediate-frequency signal 611 of a frequency of 219.050 MHz is generated by means of the oscillator 605. This frequency is the sum of the modulation frequency of 219 MHz and a small difference frequency $\Delta f$ of 50 kHz. Subsequently, the detector signal 600 is multiplied by the intermediate-frequency signal 611 in a first multiplier circuit 602 and the reference signal 601 is multiplied by the intermediate frequency signal 611 in a second multiplier circuit 603. The two signals 607, 608 are applied to a phasemeter, 609 for example of the type HP 3575A available from Hewlett Packard, via a first low-pass filter 604 and a second low-pass filter 606. The phasemeter 609 determines the phase of the low-frequency signal 607 relative to the low-frequency signal 608. This phase is available as a voltage on the terminal 610.

FIG. 7 shows the improved phase detection unit which can be included in the signal processing unit 521. In the circuit the first intermediate-frequency signal 716 is coupled to the frequency of the reference signal 701. To this end, the reference signal 701 which has a frequency of, for example approximately 219 MHz, is multiplied, in the first multiplier circuit 711 by a second intermediate-frequency signal 717 having a frequency amounting to approximately three times the frequency of the reference signal, so 654 MHz in this case. The second intermediate-frequency signal 717 is generated in the oscillator circuit 705. Via a low-pass filter 712, only the low-frequency difference signal 718, having a frequency of approximately 435 MHz, is applied to a second multiplier circuit 713. In the second multiplier circuit 713 the low-frequency difference signal 718 is multiplied again by a third intermediate-frequency signal 719 of a frequency of 654.0004 MHz which is generated in the second oscillator circuit 715. The frequency of the third intermediate-frequency signal 719 equals the sum of the frequency of the second intermediate-frequency signal 717 and a small difference frequency $\Delta f$ of 0.4 kHz. Via a second low-pass filter 714, the low-frequency difference signal of a frequency of approximately 219.0004 MHz is obtained. This signal, which follows a small frequency variation of the amplitude modulation of the laser, is used as the first intermediate-frequency signal 716 in the known phase detection unit described with reference to FIG. 6. Therein, the detector signal 700 and the reference signal 701 are multiplied by the first intermediate-frequency signal 716 in a third multiplier circuit 702 and a fourth multiplier circuit 703. Via the low-pass filters 704 and 706, the two difference signals 707 and 708, both having a frequency of approximately 50 kHz, are applied to the phasemeter 709 which is, for example of said type HP 3575A. The phase is then available as a voltage on the terminal 710. The small frequency difference of 0.4 kHz of the third intermediate frequency compared to the 50 kHz of the conventional detector, described in FIG. 6, offers the advantage of a better signal to noise ratio and hence a higher accuracy of the phase measurement.

The improved detection unit can be used in the signal processing unit of the set-up described, for example with reference to FIG. 5. The magnitude of the phase deviation, and hence the sensitivity of the phase measurement in a device utilizing two photon density waves in phase opposition, is determined by the steepness of the phase transition. This phase transition can be measured in conformity with the diagrammatic set-up shown in FIG. 8.

Figure 8:
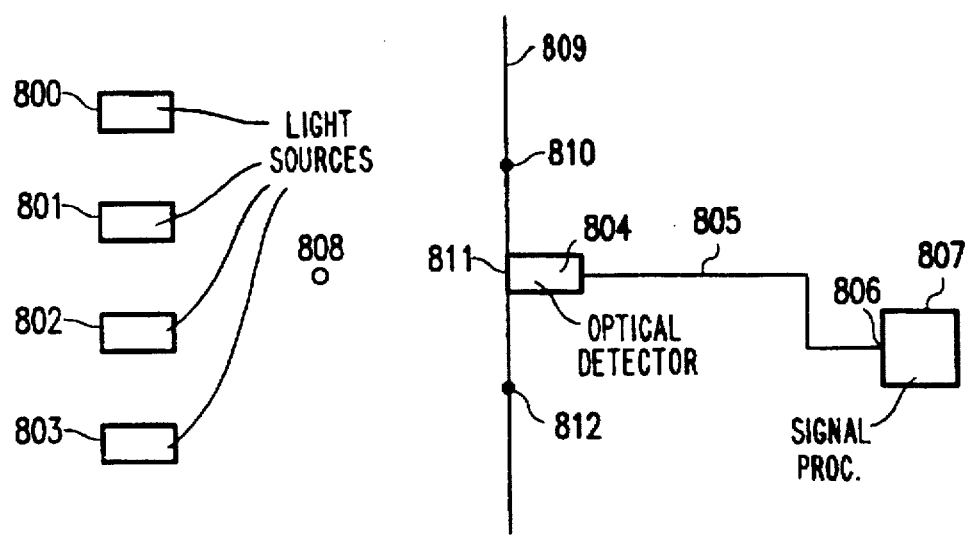
FIG. 8 shows diagrammatically the measuring device.

FIG. 8 shows diagrammatically the four light sources 800, 801, 802 and 803, and the detector aperture 804 of an optical conductor 805, the end 806 of which is coupled to the signal processing unit 807. The first light source 800 and the second light source 801 generate a first photon density wave and the third light source 802 and the fourth light source 803 generate a second photon density wave which is in phase opposition with the first photon density wave. The operation of detector 804 is arranged so as to be displaceable in small steps along a line 809 parallel to the light sources 800, 801,802 and 803 in the turbid medium. After each step the phase of the photon density wave is measured at the area of the detector aperture.

Figure 9:
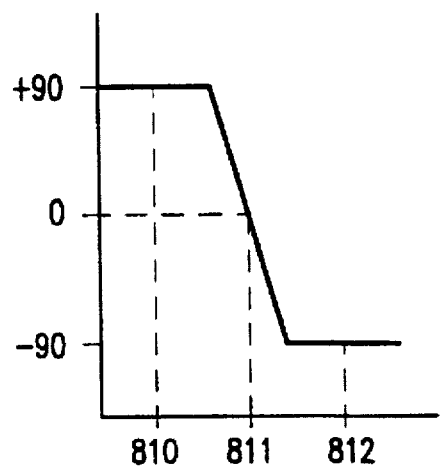
FIG. 9 shows an example of a phase transition between two photon density waves.

FIG. 9 shows diagrammatically a graph 900 of the phase measured. On the x-axis the position of the detector along the line 809 is plotted. The measured phase of the detector signal is plotted on the y-axis. When the operation of detector 804 approaches the position 810, the phase is determined mainly by the second photon density wave, so that a maximum phase is measured. When the aperture of detector 804 is in the position 811, the measured phase becomes equal to the mean value of the two photon density waves. When the detector aperture 804 is in the position 812, the phase is determined by the second photon density wave, so that a minimum value of the phase is measured.

When the aperture of detector 804 is moved to the position 811 and subsequently an object 808 is introduced into the turbid medium, between the light sources 800, 801,802, 803 and the aperture of detector 804, a phase deviation will be measured, which deviates from the phase as is shown in FIG. 9. The phase deviation is related to the scattering coefficient of the object 808. The smallest phase deviation that can be measured is determined by the sensitivity of the measurement and hence by the steepness of the phase transition. The improvement of the phase measurement in accordance with the invention, therefore, also becomes apparent upon comparison of the phase transitions of the known set-up shown of FIG. 2 and of the device in accordance with the invention.

Figure 10:
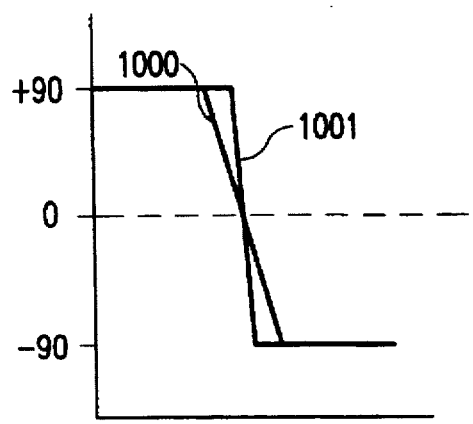
FIG. 10 shows a difference between two phase transitions.

FIG. 10 shows two phase transitions between photon density waves in phase opposition. The first phase transition 1000 has been measured by means of the known set-up, for example as described, with reference to FIG. 2. The second phase transition 1001 has been measured by means of the set-up in accordance with the invention, utilizing the amplitude-modulated laser with strong higher harmonic suppression and also the improved detection unit. FIG. 10 shows that the steepness of the second phase transition 1001 exceeds that of the first phase transition 1000, so that the sensitivity of the phase measurement in the set-up in accordance with the invention is higher.

In addition to the experimental set-up of the light sources as described in the present Application, the light sources can also be arranged in set-ups which are better suitable for the envisaged use in a medical environment, and which are also adapted to the anatomy of the biological tissue, for example the female breast or the neonatal infant's head.

Finally, for the localization of an object use can also be made of a device in which only the phase transition between the two photon density waves is shifted and the light sources 800, 801, 802, 803, the aperture of detector 804 and the object 808 are in fixed positions. To this end, for example the optical beam splitter 506 in FIG. 5 is replaced by a controllable optical beam splitter. The controllable optical beam splitter is capable of adjusting the intensity of the in-phase light sources 800, 801 relative to the intensity of the light sources 802, 803 in phase opposition, the phase transition between the photon density waves then being shifted relative to the detector aperture 804. By variation of the intensity of the first group of light sources 800, 801 between a minimum and a maximum value, the phase transition is shifted between a first position and a second position along a line 809 extending parallel to the light sources 800, 801, 802, 803. Using the stationary detector 807, a reference phase variation can be measured as a function of the intensity of the first group of light sources. An object 808 with a deviating scattering coefficient and present in the turbid medium between the light sources 800, 801, 802, 803 and the detector aperture 804 will then cause a phase deviation relative to the reference phase variation, thus enabling localization of the object.

Another possibility to control the light power of one or both light sources is formed by the application of controllable optical power devices in one or both optical conductors, which ends of the optical conductors form the light sources. The controllable optical power device comprises of a polymer Liquid Crystal Device (LCD) and two collimating lenses. The polymer LCD is placed between the collumating lenses. The polymer LCD acts as a variable aperture. When no voltage is applied to the polymer LCD, the polymer LCD strongly scatters the light, so hardly no light is transmitted through the polymer LCD. When a voltage is applied the LCD transmits up to 90% of the incoming light power. Further polymer LCD's require an AC-driving voltage, for example an AC-voltage of 30V and a frequency of 1 KHz. AM-modulation of the AC-driving voltage could control the transmitted light power and consequently the light power of the light source.

I claim:

1. A device for localizing an object in a turbid medium, comprising a laser for generating radiation which is amplitude modulated with a modulation frequency, and a detection unit for measuring the amplitude-modulated radiation from the turbid media, wherein the laser includes means for suppressing higher harmonics in the amplitude-modulated radiation.

2. A device as claimed in claim 1, wherein the laser is a laser having two laser modes and the modulation frequency equals a difference frequency between the two laser modes.

3. A device as claimed in claim 2, further comprising means for generating a phase reference from the laser radiation.

4. A device as claimed in claim 3, wherein the harmonics suppressing means is formed by at least one etalon.

5. A device as claimed in claim 4, further comprising optical beam spitters for creating secondary radiation sources from the laser radiation.

6. A device as claimed in claim 2, wherein the harmonics suppressing means is formed by at least one etalon.

7. A device as claimed in claim 2, further comprising optical beam spitters for creating secondary radiation sources from the laser radiation.

8. A device as claimed in claim 7, wherein an optical path difference between two of said secondary radiation sources induces a phase shift between said two secondary radiation sources.

9. A device as claimed in claim 1, further comprising means for generating a phase reference from the laser radiation.

10. A device as claimed in claim 9, wherein the detection unit further includes an intermediate-frequency signal is derived from the phase reference.

11. A device as claimed in 9, wherein the harmonics suppressing means is formed by at least one etalon.

12. A device as claimed in claim 9, further comprising optical beam spitters for creating secondary radiation sources from the laser radiation.

13. A device as claimed in claim 12, wherein an optical path difference between two of said secondary radiation sources induces a phase shift between said two secondary radiation sources.

14. A device as claimed in claim 1, wherein harmonics suppressing means is formed by at least one etalon.

15. A device as claimed in claim 14, further comprising optical beam spitters for creating secondary radiation sources from the laser radiation.

16. A device as claimed in claim 15, wherein an optical path difference between two of said secondary radiation sources induces a phase shift between said two secondary radiation sources.

17. A device as claimed in claim 1, further comprising optical beam spitters for creating secondary radiation sources from the laser radiation.

18. A device as claimed in claim 17, wherein an optical path difference between two of said secondary radiation sources induces a phase shift between said two secondary radiation sources.

19. A device as claimed in claim 18, wherein the secondary radiation sources are subdivided into a first group and a second group, the amplitude modulation of the radiation to be generated by the first group of radiation sources exhibit a phase difference relative to the amplitude modulation of the radiation to he generated by the second group of radiation sources.

20. A device as claimed in claim 17, wherein the secondary radiation sources are formed by optical conductor ends coupled to the optical beam spitters.

* * * * *